US010449091B2

(12) United States Patent
Angeley et al.

(10) Patent No.: US 10,449,091 B2
(45) Date of Patent: Oct. 22, 2019

(54) METHOD AND APPARATUS FOR AUTOMATED PLACEMENT OF SCANNED LASER CAPSULORHEXIS INCISIONS

(71) Applicant: OPTIMEDICA CORPORATION, Santa Ana, CA (US)

(72) Inventors: David G. Angeley, Charlotteville, VA (US); Phillip H. Gooding, Mountain View, CA (US); Bruce Woodley, Palo Alto, CA (US); George R. Marcellino, Santa Cruz, CA (US)

(73) Assignee: OPTIMEDICA CORPORATION, Santa Ana, CA (US)

( * ) Notice: Subject to any disclaimer, the term of this patent is extended or adjusted under 35 U.S.C. 154(b) by 0 days.

(21) Appl. No.: 15/294,436

(22) Filed: Oct. 14, 2016

(65) Prior Publication Data

US 2017/0027756 A1 Feb. 2, 2017

Related U.S. Application Data

(63) Continuation of application No. 14/450,587, filed on Aug. 4, 2014, now Pat. No. 9,495,743, which is a
(Continued)

(51) Int. Cl.
*G06T 7/00* (2017.01)
*A61F 9/009* (2006.01)
(Continued)

(52) U.S. Cl.
CPC .......... *A61F 9/00825* (2013.01); *A61B 3/102* (2013.01); *A61B 3/107* (2013.01);
(Continued)

(58) Field of Classification Search
CPC .............. A61F 9/008; A61F 2009/0087; A61F 2009/00872; A61F 2009/00851; A61B 3/107
See application file for complete search history.

(56) References Cited

U.S. PATENT DOCUMENTS 5,459,570 A 10/1995 Swanson et al.
5,720,894 A 2/1998 Neev et al.
(Continued)

FOREIGN PATENT DOCUMENTS

CN 201320219 Y 10/2009
CN 101631522 A 1/2010
(Continued)

OTHER PUBLICATIONS

European Search Report for Application No. EP16190432, dated Feb. 3, 2017, 7 pages.
(Continued)

*Primary Examiner* — Scott Luan
(74) *Attorney, Agent, or Firm* — Johnson & Johnson Surgical Vision, Inc.

(57) ABSTRACT

Systems and methods are described for cataract intervention. In one embodiment a system comprises a laser source configured to produce a treatment beam comprising a plurality of laser pulses; an integrated optical system comprising an imaging assembly operatively coupled to a treatment laser delivery assembly such that they share at least one common optical element, the integrated optical system being configured to acquire image information pertinent to one or more targeted tissue structures and direct the treatment beam in a 3-dimensional pattern to cause breakdown in at least one of the targeted tissue structures; and a controller operatively coupled to the laser source and integrated optical system, and configured to adjust the laser beam and treatment pattern based upon the image information, and distinguish two or more anatomical structures of the eye based at least in part upon a robust least squares fit analysis of the image information.

19 Claims, 13 Drawing Sheets

Related U.S. Application Data continuation of application No. 13/011,807, filed on Jan. 21, 2011, now Pat. No. 8,845,625.

(60) Provisional application No. 61/297,624, filed on Jan. 22, 2010.

(51) Int. Cl.
*A61B 3/107* (2006.01)
*A61B 3/10* (2006.01)
*A61F 9/008* (2006.01)
*G06T 7/13* (2017.01)
*G06T 7/149* (2017.01)
*A61B 5/00* (2006.01)

(52) U.S. Cl.
CPC .............. *A61F 9/008* (2013.01); *A61F 9/009* (2013.01); *A61F 9/0084* (2013.01); *G06T 7/0012* (2013.01); *G06T 7/13* (2017.01); *G06T 7/149* (2017.01); *A61B 5/0066* (2013.01); *A61F 2009/0087* (2013.01); *A61F 2009/00851* (2013.01); *A61F 2009/00865* (2013.01); *A61F 2009/00872* (2013.01); *A61F 2009/00876* (2013.01); *A61F 2009/00889* (2013.01); *A61F 2009/00897* (2013.01); *G06T 2207/10101* (2013.01); *G06T 2207/30041* (2013.01)

(56) References Cited

U.S. PATENT DOCUMENTS

| | | | |
|---|---|---|---|
| 5,748,352 | A | 5/1998 | Hattori |
| 5,748,898 | A | 5/1998 | Ueda |
| 5,957,915 | A | 9/1999 | Trost |
| 5,984,916 | A | 11/1999 | Lai |
| 6,019,472 | A | 2/2000 | Koester et al. |
| 6,053,613 | A | 4/2000 | Wei et al. |
| 6,079,831 | A | 6/2000 | Sarver et al. |
| 6,111,645 | A | 8/2000 | Tearney et al. |
| 6,454,761 | B1 | 9/2002 | Freedman |
| 7,655,002 | B2 | 2/2010 | Myers et al. |
| 7,717,907 | B2 | 5/2010 | Ruiz et al. |
| 8,262,646 | B2 | 9/2012 | Frey et al. |
| 8,350,183 | B2 | 1/2013 | Vogel et al. |
| 8,382,745 | B2 | 2/2013 | Naranjo-Tackman et al. |
| 8,414,564 | B2 | 4/2013 | Goldshleger et al. |
| 8,845,625 | B2 | 9/2014 | Angeley et al. |
| 2003/0223037 | A1 | 12/2003 | Chernyak |
| 2006/0104516 | A1 | 5/2006 | Lee et al. |
| 2007/0292037 | A1 | 12/2007 | Allon et al. |
| 2008/0281303 | A1 | 11/2008 | Culbertson et al. |
| 2009/0137993 | A1 | 5/2009 | Kurtz |
| 2009/0185191 | A1 | 7/2009 | Boppart et al. |
| 2010/0022995 | A1* | 1/2010 | Frey ................ A61F 9/008 606/4 |
| 2010/0324543 | A1* | 12/2010 | Kurtz ............... A61F 9/008 606/6 |
| 2011/0319873 | A1 | 12/2011 | Raksi et al. |
| 2011/0319875 | A1 | 12/2011 | Loesel et al. |

FOREIGN PATENT DOCUMENTS

| | | |
|---|---|---|
| EP | 1835861 | 9/2007 |
| EP | 1961374 A1 | 8/2008 |
| JP | 2003505178 A | 2/2003 |
| JP | 2005536236 A | 12/2005 |
| JP | 2006181358 | 7/2006 |
| WO | 02064031 A2 | 8/2002 |
| WO | 02064831 A2 | 8/2002 |
| WO | 03011764 A2 | 2/2003 |
| WO | 2008112292 A1 | 9/2008 |
| WO | 2009039315 A2 | 3/2009 |
| WO | 2009059251 A2 | 5/2009 |

OTHER PUBLICATIONS

International Search Report and Written Opinion for Application No. PCT/US2011/022158, dated May 20, 2011, 10 pages.
Liu Y., et al., "Contrast Enhancement of Optical Coherence Tomography Images Using Least Squares Fitting and Histogram Matching," Optics Communications, 2007, vol. 279 (1), pp. 23-26.

* cited by examiner

```
SUMMARY FOR CAMERA ON BB1
           SCALE:    11.572    um/PIXEL (WATER)
  CENTER OF UF BEAM X   514    PIXELS
                    Y   525    PIXELS
  ROTATION OF UF CROSS  0.673  DEG CW
```

METHOD AND APPARATUS FOR AUTOMATED PLACEMENT OF SCANNED LASER CAPSULORHEXIS INCISIONS

RELATED APPLICATION DATA

This application is a continuation of and claims priority to U.S. patent application Ser. No. 14/450,587, filed Aug. 4, 2014, which is a continuation of U.S. patent application Ser. No. 13/011,807, filed Jan. 21, 2011, which claims the benefit under 35 U.S.C. § 119 to U.S. provisional patent application Ser. No. 61/297,624 filed Jan. 22, 2010. The foregoing applications are hereby incorporated by reference into the present application in their entirety.

FIELD OF THE INVENTION

The present invention relates to ophthalmic surgical procedures and systems.

BACKGROUND OF THE INVENTION

Intraocular lens implantation is one of the most commonly performed surgical procedures in the world with an estimated 14 million cases annually performed worldwide.

Modern surgery is typically performed using a technique termed phacoemulsification in which an ultrasonic tip with an associated water stream for cooling purposes is used to sculpt the relatively hard nucleus of the lens after performance of an opening in the anterior lens capsule termed anterior capsulotomy or more recently capsulorhexis. Following these steps as well as removal of residual softer lens cortex by aspiration methods without fragmentation, a synthetic foldable intraocular lens (IOL) is inserted into the eye through a small incision.

One of the earliest and most critical steps in the procedure is the performance of the capsulotomy (or capsulorhexis). This step evolved from an earlier technique termed can-opener capsulotomy in which a sharp needle was used to perforate the anterior lens capsule in a circular fashion followed by the removal of a circular fragment of lens capsule typically in the range of 5-8 mm in diameter. Due to a variety of complications associated with the initial can-opener technique, attempts were made by leading experts in the field to develop a better technique for removal of the anterior lens capsule preceding the emulsification step. The concept of the capsulorhexis is to provide a smooth continuous circular opening through which not only the phacoemulsification of the nucleus can be performed safely and easily, but also for easy insertion of the intraocular lens. It provides both a clear central access for insertion, a permanent aperture for transmission of the image to the retina by the patient, and also a support of the IOL inside the remaining capsule that would limit the potential for dislocation. Using the older technique of can-opener capsulotomy, or even with the continuous capsulorhexis, problems may develop related to inability of the surgeon to adequately visualize the capsule due to lack of red reflex, to grasp it with sufficient security, to tear a smooth circular opening of the appropriate size without radial rips and extensions or technical difficulties related to maintenance of the anterior chamber depth after initial opening, small size of the pupil, or the absence of a red reflex due to the lens opacity. Some of the problems with visualization have been minimized through the use of dyes such as methylene blue or indocyanine green. However, visualization of the capsule is but one issue.

The orientation of the eye can also cause problems for the surgeon, as the capsulorhexis incision may be made off-center if parallax error is introduced by the stereoscopic imaging system. Additional complications arise in patients with weak zonules (typically older patients) and very young children that have very soft and elastic capsules, which are very difficult to mechanically rupture.

What is needed are ophthalmic methods, techniques and apparatus to advance the standard of care for the accurate and reliable placement of ocular incisions such as paracentesis, cataract instrument access, relaxing, and capsulotomy.

SUMMARY OF THE INVENTION

One embodiment is directed to a system for cataract surgery on an eye of a patient, comprising a laser source configured to produce a treatment beam comprising a plurality of laser pulses; an integrated optical system comprising an imaging assembly operatively coupled to a treatment laser delivery assembly such that they share at least one common optical element, the integrated optical system being configured to acquire image information pertinent to one or more targeted tissue structures and direct the treatment beam in a 3-dimensional pattern to cause breakdown in at least one of the targeted tissue structures; and a controller operatively coupled to the laser source and integrated optical system, and configured to adjust the laser beam and treatment pattern based upon the image information, and distinguish two or more anatomical structures of the eye based at least in part upon a robust least squares fit analysis of the image information. One of the two or more anatomical structures comprises a cornea, a sclera, a limbus, an iris, a lens, or a lens capsule. The controller may be configured to conduct a series of least squares fit analyses, and to iteratively include a greater number of pixels in each successive least squares fit analysis. The controller may be configured to find a close least squares fit where the pertinent least squares fit analysis expects a spherical surface. The controller may be configured to find a close least squares fit where the pertinent least squares fit analysis expects an aspherical surface. The controller may be further configured to locate a boundary between the two or more anatomical structures. The boundary may be defined as the intersection between a cornea of the eye and a sclera of the eye. The boundary may be defined as the intersection between a cornea of the eye and an iris of the eye. The boundary may be defined as the intersection between a lens of the eye and an iris of the eye. The controller may be configured to utilize rejected points of a least squares fit analyses to identify an anatomical structure of the eye.

Another embodiment is direct to a system further comprising an adjustable focus assembly to allow for imaging of the retina that provides information regarding the location of the fovea and/or the foveola centralis to determine the visual axis of a patient. Such retinal features may be identified via image information from the imaging device and used in conjunction with geometric information about the lens to provide for augmented capsulotomy pattern placement. The imaging device may provide either 3D or a 2D images, or both.

Another embodiment is directed to a system further configured to provide the user with the choice of using any one of the abovementioned fits to place the laser created incisions. For example, the video system may display an en-face image of the patient's eye with the limbal, geometric, and visual centering results overlaid. The user may then choose the method based upon its appearance with respect to the video image. Similarly, the system may display the intended location(s) of corneal incisions for the user to choose.

In yet another embodiment, the system further comprises a second imaging system, such as a video system. Both the OCT and video systems can be used to guide the laser incisions. For example, the center of the pupil can be determined by simultaneously considering both the OCT and the video system data to determine if a pixel or eye location is a pupil or non-pupil pixel. For a location to be deemed as within the pupil, it may be required that both systems independently discern this conclusion. Alternatively, the location can be within the pupil if at least one system comes to this conclusion.

Another embodiment is directed to an optical system comprising an adjustable light source for exposing the eye of a patient to variable lighting conditions, or levels of brightness, and an imaging device, such as a video camera, to capture images of the eye to determine the size, shape, position and registration marks or anatomic fiducials of the pupil in order to best determine the appropriate lateral location for creating a laser capsulotomy incision.

The techniques and systems disclosed herein provide many advantages over the current standard of care. Specifically, the image guided alignment of a capsulorhexis incision. The techniques described herein may be used to facilitate implantation intraocular lenses (IOLs), including bag-in-lens and lens-in-bag types. The incision is not limited only to circular but may be any shape that is conducive to follow on procedures such as, for example, injection or formation of complex or advanced IOL devices or fixed accommodating IOLs. Other objects and features of the present invention will become apparent by a review of the specification, claims and appended figures.

DETAILED DESCRIPTION OF THE PREFERRED EMBODIMENTS

Figure 1:
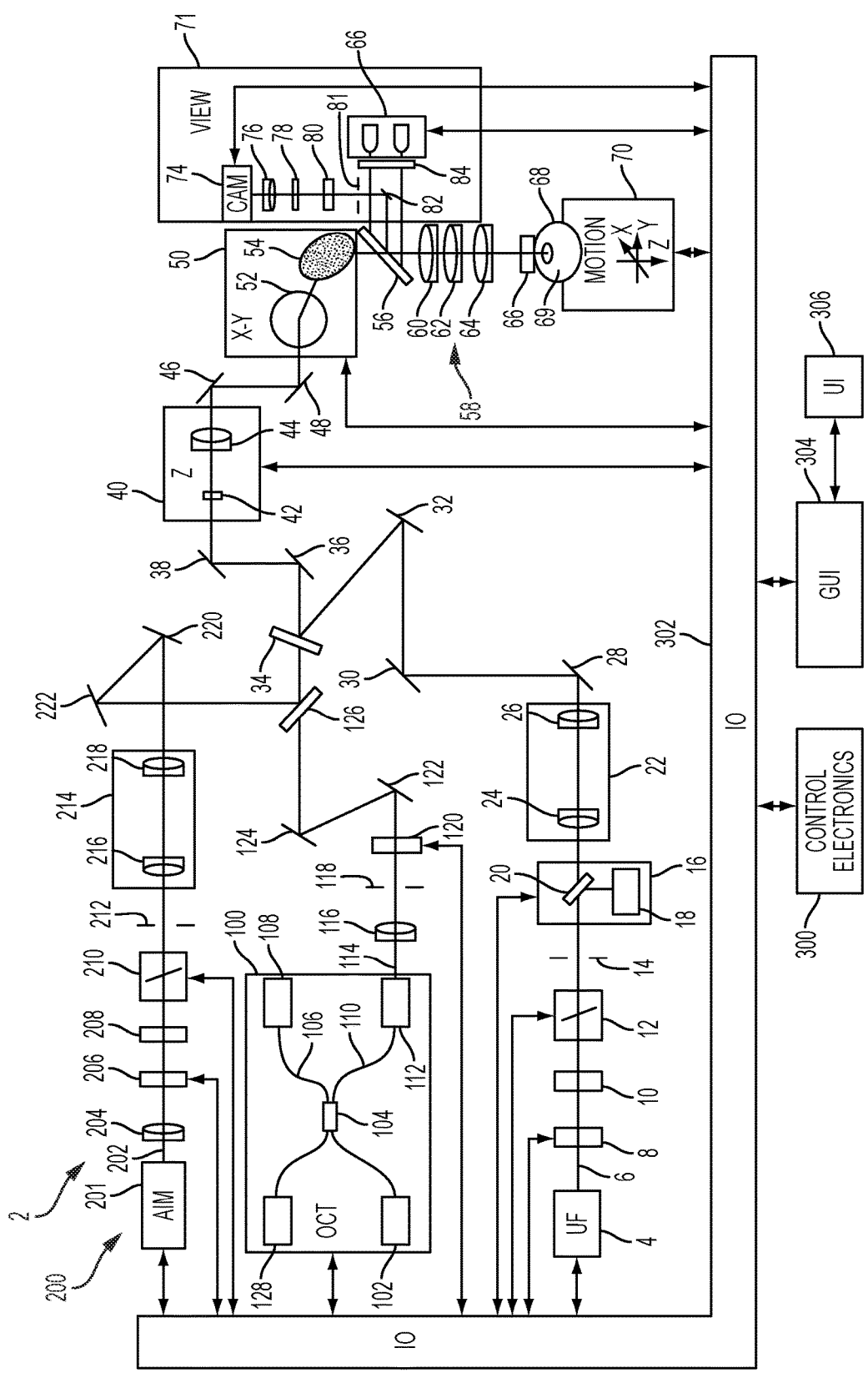
FIG. 1 is a schematic diagram of the optical beam scanning system.

The present invention can be implemented by a system that projects or scans an optical beam into a patient's eye 68, such as system 2 shown in FIG. 1 which includes an ultrafast (UF) light source 4 (e.g. a femtosecond laser). Using this system, a beam may be scanned in a patient's eye in three dimensions: X, Y, Z. In this embodiment, the UF wavelength can vary between 1010 nm to 1100 nm and the pulse width can vary from 100 fs to 10000 fs. The pulse repetition frequency can also vary from 10 kHz to 250 kHz. Safety limits with regard to unintended damage to non-targeted tissue bound the upper limit with regard to repetition rate and pulse energy; while threshold energy, time to complete the procedure and stability bound the lower limit for pulse energy and repetition rate. The peak power of the focused spot in the eye 68 and specifically within the crystalline lens 69 and anterior capsule of the eye is sufficient to produce optical breakdown and initiate a plasma-mediated ablation process. Near-infrared wavelengths are preferred because linear optical absorption and scattering in biological tissue is reduced across that spectral range. As an example, laser 4 may be a repetitively pulsed 1035 nm device that produces 500 fs pulses at a repetition rate of 100 kHz and individual pulse energy in the ten microjoule range.

The laser 4 is controlled by control electronics 300, via an input and output device 302, to create optical beam 6. Control electronics 300 may be a computer, microcontroller, etc. In this example, the entire system is controlled by the controller 300, and data moved through input/output device IO 302. A graphical user interface GUI 304 may be used to set system operating parameters, process user input (UI) 306 on the GUI 304, and display gathered information such as images of ocular structures.

The generated UF light beam 6 proceeds towards the patient eye 68 passing through half-wave plate, 8, and linear polarizer, 10. The polarization state of the beam can be adjusted so that the desired amount of light passes through half-wave plate 8 and linear polarizer 10, which together act as a variable attenuator for the UF beam 6. Additionally, the orientation of linear polarizer 10 determines the incident polarization state incident upon beamcombiner 34, thereby optimizing beamcombiner throughput.

The UF beam proceeds through a shutter 12, aperture 14, and a pickoff device 16. The system controlled shutter 12 ensures on/off control of the laser for procedural and safety reasons. The aperture sets an outer useful diameter for the laser beam and the pickoff monitors the output of the useful beam. The pickoff device 16 includes of a partially reflecting mirror 20 and a detector 18. Pulse energy, average power, or a combination may be measured using detector 18. The information can be used for feedback to the half-wave plate 8 for attenuation and to verify whether the shutter 12 is open or closed. In addition, the shutter 12 may have position sensors to provide a redundant state detection.

The beam passes through a beam conditioning stage 22, in which beam parameters such as beam diameter, divergence, circularity, and astigmatism can be modified. In this illustrative example, the beam conditioning stage 22 includes a 2 element beam expanding telescope comprised of spherical optics 24 and 26 in order to achieve the intended beam size and collimation. Although not illustrated here, an anamorphic or other optical system can be used to achieve the desired beam parameters. A zoom or reverse telephoto lens system may be used, by way of further example. The factors used to determine these beam parameters include the output beam parameters of the laser, the overall magnification of the system, and the desired numerical aperture (NA) at the treatment location. These conditioning optical elements may be dynamic or adjustable either one time manually or automatically. An example of a dynamic element would be a zoom beam expander that would enable the adjustment of focal length and magnification. Such a variable zoom could be used to decrease or increase the beam diameter of the laser beam entering into the final focusing objective and therefore increase and decrease the NA at the treatment location. A variable feature such as this may be useful in dertermining the plasma threshold level and may further be used as compensation for other parameters that affect threshold. These other parameters may be beam quality of the laser ($M^2$), pulse duration of the laser, and transmission of the beam train. The ability to vary the NA and therefore threshold levels is advantageous to creating effective cuts throughout the intended cutting volume. This dialing in of the threshold could be a one-time adjustment per laser per system to create an overhead margin in creating cuts throughout the volume or it could be adjusted on the fly, i.e. at a high enough rate so that the threshold value can be change while cutting the pattern and depending on the location of the cut for example.

In addition, the optical system 22 can be used to image aperture 14 to a desired location (e.g. the center location between the 2-axis scanning device 50 described below). In this way, the amount of light that makes it through the aperture 14 is assured to make it through the scanning system. Pickoff device 16 is then a reliable measure of the usable light. Alternatively, if the beam location at the aperture is reliable and stable, the aperture can be placed after the pickoff device. In this way the system maybe made shorter, reducing the beam path footprint. After exiting conditioning stage 22, beam 6 reflects off of fold mirrors 28, 30, & 32. These mirrors can be adjustable for alignment purposes. The beam 6 is then incident upon beam combiner 34. Beamcombiner 34 reflects the UF beam 6 (and transmits both the OCT 114 and aim 202 beams described below). For efficient beamcombiner operation, the angle of incidence is preferably kept below 45 degrees and the polarization where possible of the beams is fixed. For the UF beam 6, the orientation of linear polarizer 10 provides fixed polarization.

Following the beam combiner 34, the beam 6 continues onto the z-adjust or Z scan device 40. In this illustrative example the z-adjust includes a Galilean telescope with two lens groups 42 and 44 (each lens group includes one or more lenses). Lens group 42 moves along the z-axis about the collimation position of the telescope. In this way, the focus position of the spot in the patient's eye 68 moves along the z-axis as indicated. In general there is a fixed relationship between the motion of lens 42 and the motion of the focus. In this case, the z-adjust telescope has an approximate 2× beam expansion ratio and an approximate 1:1 relationship of the movement of lens 42 to the movement of the focus. The exact relationship between the movement of the lens and the consequent z movement of the focal spot within the eye depends on the focal lengths of the lenses 42, 44, 60, 62, 64, 66, the index of refraction of the materials in the eye, the separations between at least two of these lenses, and location of the focal point. In the illustrative embodiment, the relationship is approximately 1.2:1 at focal locations near the cornea and 1.5:1 near focal positions near the posterior surface of the crystalline lens. Alternatively, lens group 44 could be moved along the z-axis to actuate the z-adjust, and scan. The z-adjust is the z-scan device for treatment in the eye 68. It can be controlled automatically and dynamically by the system and selected to be independent or to interplay with the X-Y scan device described next. Mirrors 36 and 38 can be used for aligning the optical axis with the axis of z-adjust device 40. After passing through the z-adjust device 40, the beam 6 is directed to the x-y scan device by mirrors 46 & 48. Mirrors 46 & 48 can be adjustable for alignment purposes. X-Y scanning is achieved by the scanning device 50 preferably using two mirrors 52 & 54 under the control of control electronics 300, which rotate in orthogonal directions using motors, galvanometers, or any other well known optic moving device. Mirrors 52 & 54 are located near the telecentric position of the objective lens 58 and contact lens 66 combination described below. Tilting these mirrors 52/54 causes them to deflect beam 6, causing lateral displacements in the plane of UF focus located in the patient's eye 68. Objective lens 58 may be a complex multi-element lens element, as shown, and represented by lenses 60, 62, and 64. The complexity of the lens 58 will be dictated by the scan field size, the focused spot size, the available working distance on both the proximal and distal sides of objective 58, as well as the amount of aberration control. An scan lens 58 of focal length 60 mm generating a spot size of 10 um, over a field of 10 mm, with an input beam size of 15 mm diameter is an example. Alternatively, X-Y scanning by scanner 50 may be achieved by using one or more moveable optical elements (e.g. lenses, gratings) which also may be controlled by control electronics 300, via input and output device 302.

The aiming and treatment scan patterns can be automatically generated by the scanner 50 under the control of controller 300. Such patterns may be comprised of a single spot of light, multiple spots of light, a continuous pattern of light, multiple continuous patterns of light, and/or any combination of these. In addition, the aiming pattern (using aim beam 202 described below) need not be identical to the treatment pattern (using light beam 6), but preferably at least defines its boundaries in order to assure that the treatment light is delivered only within the desired target area for patient safety. This may be done, for example, by having the aiming pattern provide an outline of the intended treatment pattern. This way the spatial extent of the treatment pattern may be made known to the user, if not the exact locations of the individual spots themselves, and the scanning thus optimized for speed, efficiency and accuracy. The aiming pattern may also be made to be perceived as blinking in order to further enhance its visibility to the user. The positioning and character of optical beam 6 and/or the scan pattern that beam 6 forms on the eye 68 may be further controlled by use of an input device such as a joystick, or any other appropriate user input device (e.g. GUI 304) to position the patient and/or the optical system.

A contact lens 66, which can be any suitable ophthalmic lens, can be used to help further focus the optical beam 6 into the patient's eye 68 while helping to stabilize eye position. The contact lens may be glass, plastic, or other suitable optical material with a solid surface contacting the cornea of the eye. The contact surface may be curved to match the surface form of the anterior of the cornea. The contact surface may also be flat or other shape that does not conform to the surface form of the cornea and thereby deform the anterior of the eye to conform to the contact lens contacting surface shape. The contact lens may also consist of a fluid layer between the solid material of the contact lens and the anterior of the cornea. This fluid could be water or other suitable optical fluid. The fluid would provide a suitable optical matching without deforming the cornea. Lastly, the system may be used without a contact lens. This mode of operation may be suitable for focusing the beam at or near the cornea where the optical power of the cornea has a negligible effect on the beam.

The UF laser 4 and controller 300 can be set to target the surfaces of the targeted structures in the eye 68 and ensure that the beam 6 will be focused where appropriate and not unintentionally damage non-targeted tissue. Imaging modalities and techniques described herein, such as for example, Optical Coherence Tomography (OCT), Purkinje imaging, Scheimpflug imaging, or ultrasound may be used to determine the location and measure the thickness of the lens and lens capsule to provide greater precision to the laser focusing methods, including 2D and 3D patterning. Laser focusing may also be accomplished using one or more methods including direct observation of an aiming beam, Optical Coherence Tomography (OCT), Purkinje imaging, Scheimpflug imaging, ultrasound, or other known ophthalmic or medical imaging modalities and/or combinations thereof. In the embodiment of FIG. 1, an OCT device 100 is described, although other modalities are within the scope of the present invention. An OCT scan of the eye will provides information about the axial location of the anterior and posterior lens capsule, as well as the depth of the anterior chamber. This information is then be loaded into the control electronics 300, and used to program and control the subsequent laser-assisted surgical procedure. The information may also be used to determine a wide variety of parameters related to the procedure such as, for example, the upper and lower axial limits of the focal surfaces used for cutting the lens capsule and segmentation of the lens cortex and nucleus, and the thickness of the lens capsule among others.

The OCT device 100 in FIG. 1 includes a broadband or a swept light source 102 that is split by a fiber coupler 104 into a reference arm 106 and a sample arm 110. The reference arm 106 includes a module 108 containing a reference reflection along with suitable dispersion and path length compensation. The sample arm 110 of the OCT device 100 has an output connector 112 that serves as an interface to the rest of the UF laser system. The return signals from both the reference and sample arms 106, 110 are then directed by coupler 104 to a detection device 128, which employs either time domain, frequency or single point detection techniques. In FIG. 1, a frequency domain technique is used with an OCT wavelength of 920 nm and bandwidth of 100 nm. Alternatively, an OCT source can be used within the 790 nm-970 nm wavelength range with a bandwidth of 10 nm to 100 nm.

Exiting connector 112, the OCT beam 114 is collimated using lens 116. The size of the collimated beam 114 is determined by the focal length of lens 116. The size of the beam 114 is dictated by the desired NA at the focus in the eye and the magnification of the beam train leading to the eye 68. Generally, OCT beam 114 does not require as high an NA as the UF beam 6 in the focal plane and therefore the OCT beam 114 is smaller in diameter than the UF beam 6 at the beamcombiner 34 location. Following collimating lens 116 is aperture 118 which further modifies the resultant NA of the OCT beam 114 at the eye. The diameter of aperture 118 is chosen to optimize OCT light incident on the target tissue and the strength of the return signal. Polarization control element 120, which may be active or dynamic, is used to compensate for polarization state changes which may be induced by individual differences in corneal birefringence, for example. Mirrors 122 & 124 are then used to direct the OCT beam 114 towards beamcombiners 126 & 34. Mirrors 122 & 124 may be adjustable for alignment purposes and in particular for overlaying of OCT beam 114 to UF beam 6 subsequent to beamcombiner 34. Similarly, beamcombiner 126 is used to combine the OCT beam 114 with the aim beam 202 described below.

Once combined with the UF beam 6 subsequent to beamcombiner 34, OCT beam 114 follows the same path as UF beam 6 through the rest of the system. In this way, OCT beam 114 is indicative of the location of UF beam 6. OCT beam 114 passes through the z-scan 40 and x-y scan 50 devices then the objective lens 58, contact lens 66 and on into the eye 68.

Reflections and scatter off of structures within the eye provide return beams that retrace back through the optical system, into connector 112, through coupler 104, and to OCT detector 128. These return back reflections provide the OCT signals that are in turn interpreted by the system as to the location in X, Y, Z of UF beam 6 focal location.

OCT device 100 works on the principle of measuring differences in optical path length between its reference and sample arms. Therefore, passing the OCT through z-adjust 40 does not extend the z-range of OCT system 100 because the optical path length does not change as a function of movement of 42. OCT system 100 has an inherent z-range that is related to the detection scheme, and in the case of frequency domain detection it is specifically related to the spectrometer and the location of the reference arm 106. In the case of OCT system 100 used in FIG. 1, the z-range may be approximately 1-2 mm in an aqueous environment. Extending this range to at least 6 mm involves the adjustment of the path length of the reference arm within OCT system 100. Passing the OCT beam 114 in the sample arm through the z-scan of z-adjust 40 allows for optimization of the OCT signal strength. This is accomplished by focusing the OCT beam 114 onto the targeted structure while accommodating the extended optical path length by commensurately increasing the path within the reference arm 106 of OCT system 100.

Because of the fundamental differences in the OCT measurement with respect to the UF focus device due to influences such as immersion index, refraction, and aberration, both chromatic and monochromatic, care must be taken in analyzing the OCT signal with respect to the UF beam focal location. A calibration or registration procedure as a function of X, Y, Z should be conducted in order to match the OCT signal information to the UF focus location and also to the relative to absolute dimensional quantities. Observation of an aim beam may also be used to assist the user to directing the UF laser focus. Additionally, an aim beam visible to the unaided eye in lieu of the infrared OCT and UF beams can be helpful with alignment provided the aim beam accurately represents the infrared beam parameters. An aim subsystem 200 is employed in the configuration shown in FIG. 1. The aim beam 202 is generated by an aim beam light source 201, such as a helium-neon laser operating at a wavelength of 633 nm. Alternatively a laser diode in the 630-650 nm range could be used. The advantage of using the helium neon 633 nm beam is its long coherence length, which would enable the use of the aim path as a laser unequal path interferometer (LUPI) to measure the optical quality of the beam train, for example.

Once the aim beam light source generates aim beam 202, the aim beam 202 is collimated using lens 204. The size of the collimated beam is determined by the focal length of lens 204. The size of the aim beam 202 is dictated by the desired NA at the focus in the eye and the magnification of the beam train leading to the eye 68. Generally, aim beam 202 should have close to the same NA as UF beam 6 in the focal plane and therefore aim beam 202 is of similar diameter to the UF beam at the beamcombiner 34 location. Because the aim beam is meant to stand-in for the UF beam 6 during system alignment to the target tissue of the eye, much of the aim path mimics the UF path as described previously. The aim beam 202 proceeds through a half-wave plate 206 and linear polarizer 208. The polarization state of the aim beam 202 can be adjusted so that the desired amount of light passes through polarizer 208. Elements 206 & 208 therefore act as a variable attenuator for the aim beam 202. Additionally, the orientation of polarizer 208 determines the incident polarization state incident upon beamcombiners 126 and 34, thereby fixing the polarization state and allowing for optimization of the beamcombiners' throughput. Of course, if a semiconductor laser is used as aim beam light source 200, the drive current can be varied to adjust the optical power.

The aim beam 202 proceeds through a shutter 210 and aperture 212.

The system controlled shutter 210 provides on/off control of the aim beam 202. The aperture 212 sets an outer useful diameter for the aim beam 202 and can be adjusted appropriately. A calibration procedure measuring the output of the aim beam 202 at the eye can be used to set the attenuation of aim beam 202 via control of polarizer 206.

The aim beam 202 next passes through a beam conditioning device 214. Beam parameters such as beam diameter, divergence, circularity, and astigmatism can be modified using one or more well known beaming conditioning optical elements. In the case of an aim beam 202 emerging from an optical fiber, the beam conditioning device 214 can simply include a beam expanding telescope with two optical elements 216 and 218 in order to achieve the intended beam size and collimation. The final factors used to determine the aim beam parameters such as degree of collimation are dictated by what is necessary to match the UF beam 6 and aim beam 202 at the location of the eye 68. Chromatic differences can be taken into account by appropriate adjustments of beam conditioning device 214. In addition, the optical system 214 is used to image aperture 212 to a desired location such as a conjugate location of aperture 14. The aim beam 202 next reflects off of fold mirrors 222 & 220, which are preferably adjustable for alignment registration to UF beam 6 subsequent to beam combiner 34. The aim beam 202 is then incident upon beam combiner 126 where the aim beam 202 is combined with OCT beam 114. Beamcombiner 126 reflects the aim beam 202 and transmits the OCT beam 114, which allows for efficient operation of the beamcombining functions at both wavelength ranges. Alternatively, the transmit and reflect functions of beamcombiner 126 can be reversed and the configuration inverted. Subsequent to beamcombiner 126, aim beam 202 along with OCT beam 114 is combined with UF beam 6 by beamcombiner 34.

A device for imaging the target tissue on or within the eye 68 is shown schematically in FIG. 1 as imaging system 71. Imaging system includes a camera 74 and an illumination light source 86 for creating an image of the target tissue. The imaging system 71 gathers images which may be used by the system controller 300 for providing pattern centering about or within a predefined structure. The illumination light source 86 for the viewing is generally broadband and incoherent. For example, light source 86 can include multiple LEDs as shown. The wavelength of the viewing light source 86 is preferably in the range of 700 nm to 750 nm, but can be anything which is accommodated by the beamcombiner 56, which combines the viewing light with the beam path for UF beam 6 and aim beam 202 (beamcombiner 56 reflects the viewing wavelengths while transmitting the OCT and UF wavelengths). The beamcombiner 56 may partially transmit the aim wavelength so that the aim beam 202 can be visible to the viewing camera 74. Optional polarization element 84 in front of light source 86 can be a linear polarizer, a quarter wave plate, a half-wave plate or any combination, and is used to optimize signal. A false color image as generated by the near infrared wavelength is acceptable. In yet another embodiment, a full color image is generated by using visible light illumination or a range of wavelengths, and a color camera, which may enhance actual or perceived diagnostic quality of the image. The illumination light from light source 86 is directed down towards the eye using the same objective lens 58 and contact lens 66 as the UF and aim beam 6, 202. The light reflected and scattered off of various structures in the eye 68 are collected by the same lenses 58 & 66 and directed back towards beamcombiner 56. There, the return light is directed back into the viewing path via beam combiner and mirror 82, and on to camera 74. Camera 74 can be, for example but not limited to, any silicon based detector array of the appropriately sized format. Video lens 76 forms an image onto the camera's detector array while optical elements 80 & 78 provide polarization control and wavelength filtering respectively. Aperture or iris 81 provides control of imaging NA and therefore depth of focus and depth of field. A small aperture provides the advantage of large depth of field which aids in the patient docking procedure. Alternatively, the illumination and camera paths can be switched. Furthermore, aim light source 200 can be made to emit in the infrared which would not directly visible, but could be captured and displayed using imaging system 71.

Coarse adjust registration is usually needed so that when the contact lens 66 comes into contact with the cornea, the targeted structures are in the capture range of the X, Y scan of the system. Therefore a docking procedure is preferred, which preferably takes in account patient motion as the system approaches the contact condition (i.e. contact between the patient's eye 68 and the contact lens 66. The viewing system 71 is configured so that the depth of focus is large enough such that the patient's eye 68 and other salient features may be seen before the contact lens 66 makes contact with eye 68. Preferably, a motion control system 70 is integrated into the overall control system 2, and may move the patient, the system 2 or elements thereof, or both, to achieve accurate and reliable contact between contact lens 66 and eye 68. Furthermore, a vacuum suction subsystem and flange may be incorporated into system 2, and used to stabilize eye 68. The alignment of eye 68 to system 2 via contact lens 66 may be accomplished while monitoring the output of imaging system 71, and performed manually or automatically by analyzing the images produced by imaging system 71 electronically by means of control electronics 300 via IO 302. Force and/or pressure sensor feedback may also be used to discern contact, as well as to initiate the vacuum subsystem.

Figure 2:
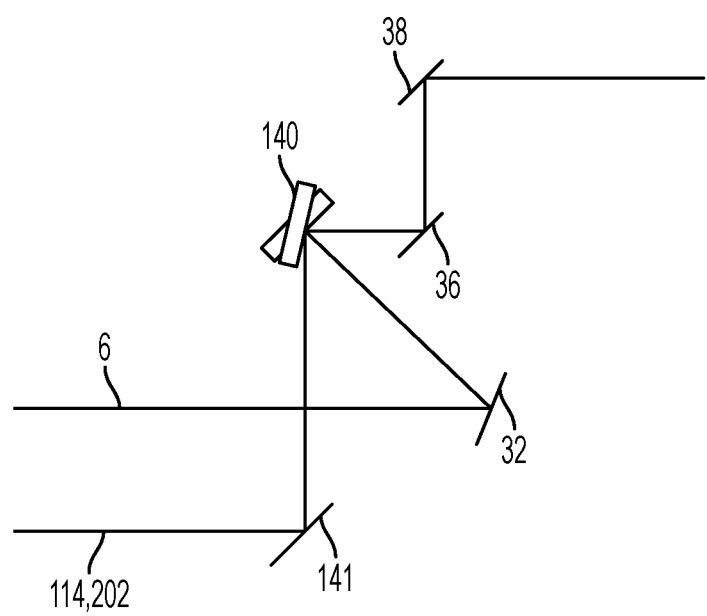
FIG. 2 is an optical diagram showing an alternative beam combining scheme.

An alternative beamcombining configuration is shown in the alternate embodiment of FIG. 2. For example, the passive beamcombiner 34 in FIG. 1 can be replaced with an active combiner 140 in FIG. 2. The active beamcombiner 34 can be a moving or dynamically controlled element such as a galvanometric scanning mirror, as shown. Active combiner 140 changes it angular orientation in order to direct either the UF beam 6 or the combined aim and OCT beams 202, 114 towards the scanner 50 and eventually eye 68 one at a time. The advantage of the active combining technique is that it avoids the difficulty of combining beams with similar wavelength ranges or polarization states using a passive beam combiner. This ability is traded off against the ability to have simultaneous beams in time and potentially less accuracy and precision due to positional tolerances of active beam combiner 140.

Figure 3:
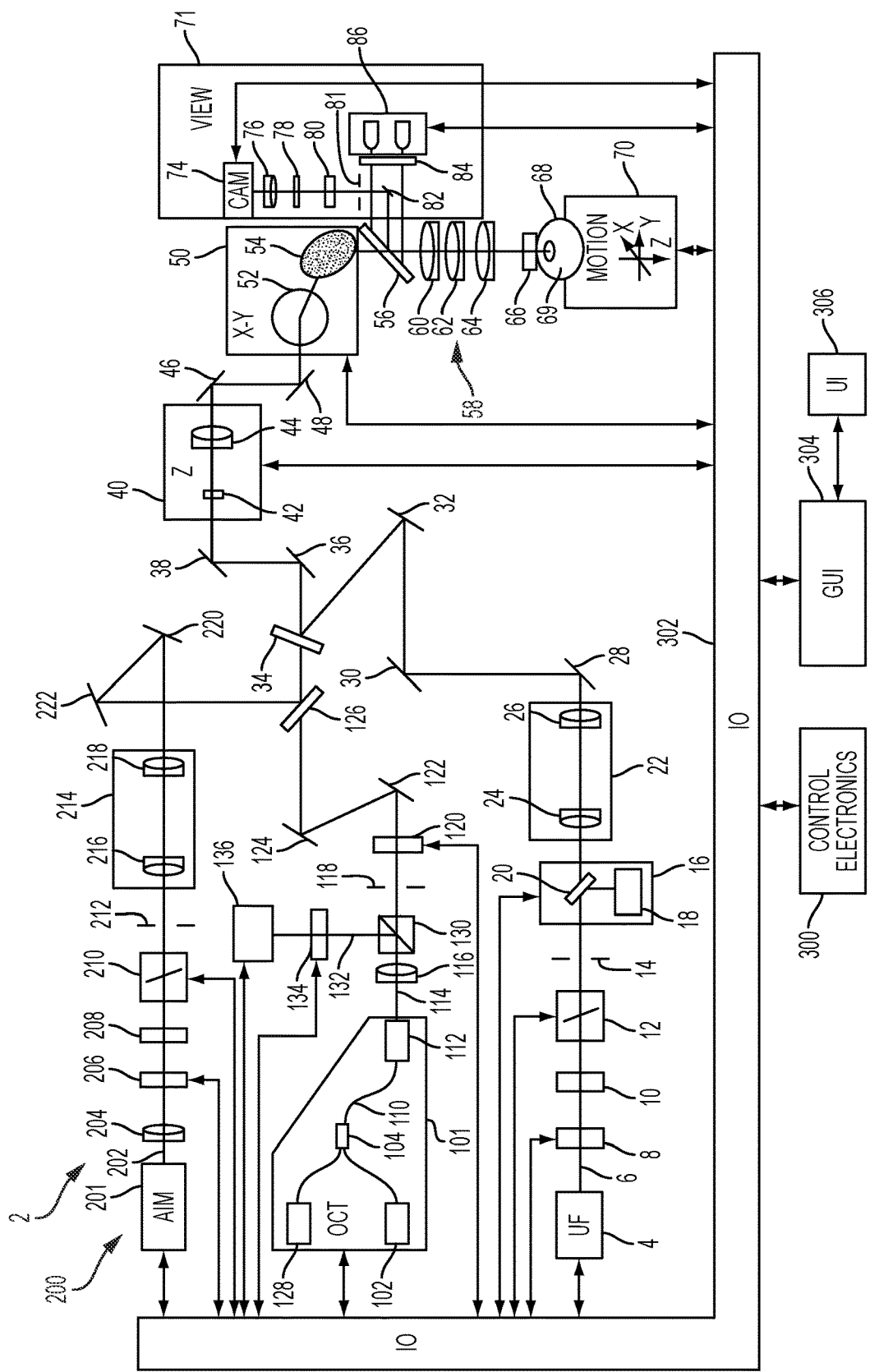
FIG. 3 is a schematic diagram of the optical beam scanning system with an alternative OCT configuration.

Another alternate embodiment is shown in FIG. 3 which is similar to that of FIG. 1 but utilizes an alternate approach to OCT 100. In FIG. 3, OCT 101 is the same as OCT 100 in FIG. 1, except that the reference arm 106 has been replaced by reference arm 132. This free-space OCT reference arm 132 is realized by including beamsplitter 130 after lens 116. The reference beam 132 then proceeds through polarization controlling element 134 and then onto the reference return module 136. The reference return module 136 contains the appropriate dispersion and path length adjusting and compensating elements and generates an appropriate reference signal for interference with the sample signal. The sample arm of OCT 101 now originates subsequent to beamsplitter 130. The potential advantages of this free space configuration include separate polarization control and maintenance of the reference and sample arms. The fiber based beam splitter 104 of OCT 101 can also be replaced by a fiber based circulator. Alternately, both OCT detector 128 and beamsplitter 130 might be moved together as opposed to reference arm 136.

Figure 4:
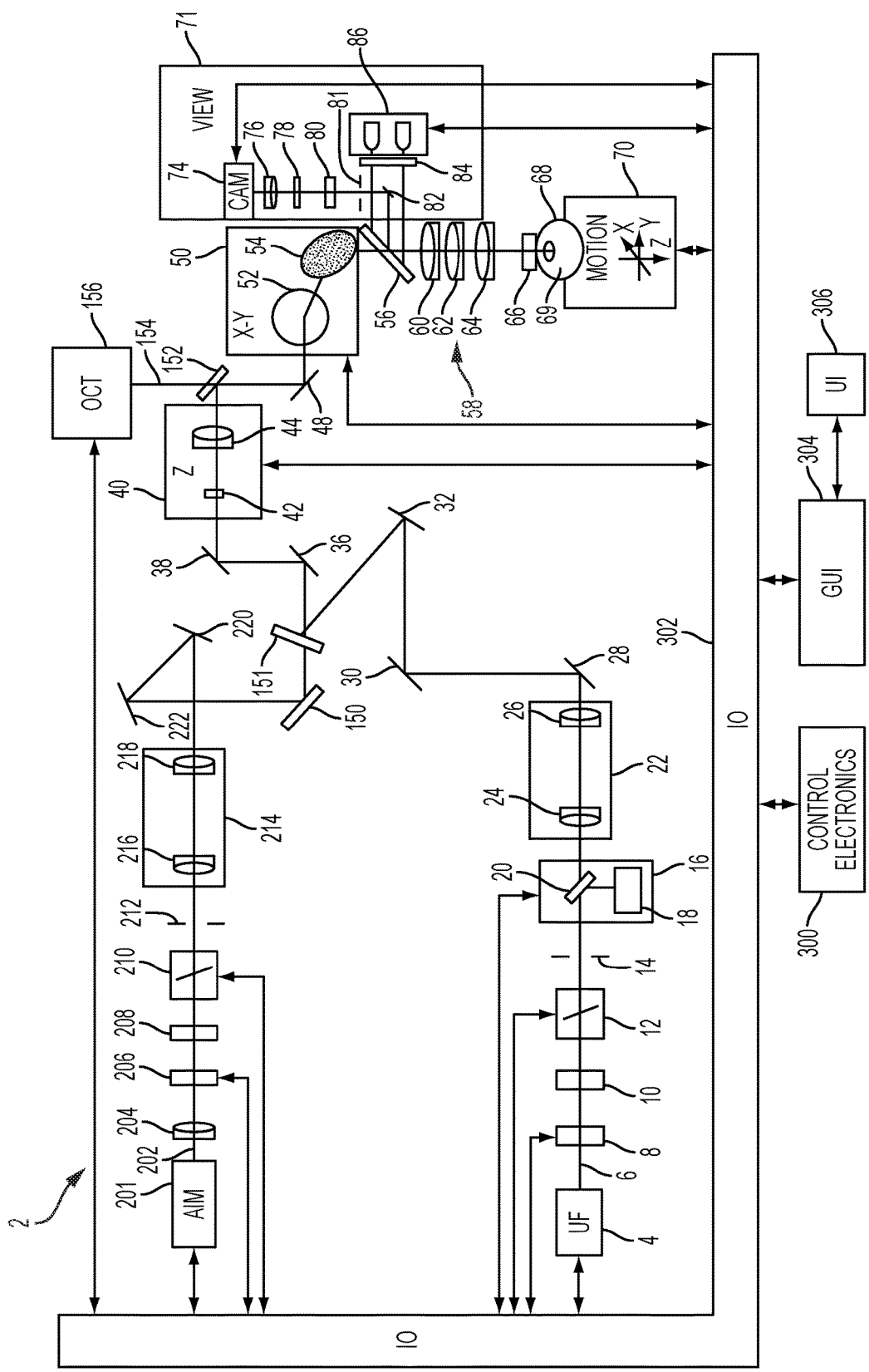
FIG. 4 is a schematic diagram of the optical beam scanning system with another alternative OCT combining scheme.

FIG. 4 shows another alternative embodiment for combining OCT beam 114 and UF beam 6. In FIG. 4, OCT 156 (which can include either of the configurations of OCT 100 or 101) is configured such that its OCT beam 154 is coupled to UF beam 6 after the z-scan 40 using beamcombiner 152. In this way, OCT beam 154 avoids using the z-adjust. This allows the OCT 156 to possibly be folded into the beam more easily and shortening the path length for more stable operation. This OCT configuration is at the expense of an optimized signal return strength as discussed with respect to FIG. 1. There are many possibilities for the configuration of the OCT interferometer, including time and frequency domain approaches, single and dual beam methods, swept source, etc, as described in U.S. Pat. Nos. 5,748,898; 5,748,352; 5,459,570; 6,111,645; and 6,053,613 (which are incorporated herein by reference.)

Figure 5:
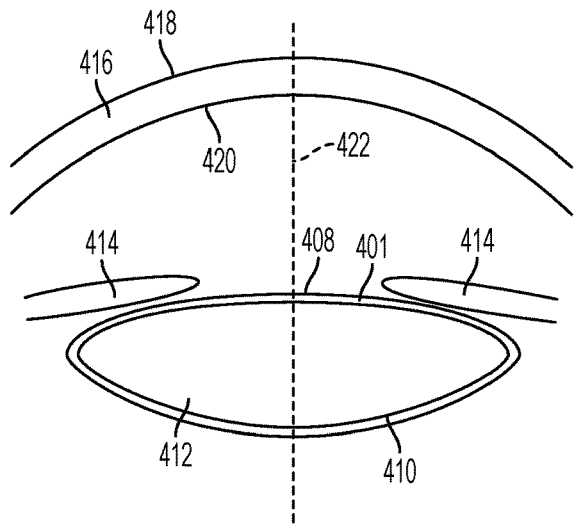
FIG. 5 is a cross-sectional schematic of the eye depicting the cornea, iris, lens, and lens capsule.

FIG. 5 is a cross-sectional schematic of the eye with various structures indicated. Each of these structures can be used as landmarks for guiding the location for the laser cuts in the capsule. These candidate landmark structures include the anterior surface 418 of the cornea 416, the posterior surface 420 of the cornea, the iris 414, the crystalline lens 412, the posterior of the lens 410, the anterior of the lens 401, and the anterior portion of the capsule 408 that surrounds the lens. Features of these structures can also be used such as radii of curvature for the cornea and lens, relative location of these surfaces, or diameter of the iris.

The structures and features of the structures may be directly measured or determined via analysis. For example, the iris boundary may be detected from an image of the iris on a detector array or video. From this boundary and proper calibration of the imaging system, the iris diameter in eye dimensions can be determined and used to determine the center location of the capsule cut as indicated by the intersection of axis 422 with the capsule 408.

Another example is the anterior surface 418 of the cornea is detected using a scanning OCT system 100. The radius of the curvature of the surface can then be determined. Likewise the radii of curvature can be found for the posterior surface 420 of the cornea and for the anterior surface 401 and posterior surface 410 of the lens. Choosing the best fit axis 422 thru the centers of these radii of curvature can be determined and this axis used to determine the location of the capsule cut. Alternatively and similarly to the video system, the OCT system can also detect the iris boundary location and calculate the center for the cut. The goal for the system is to be able to detect these landmarks or the appropriate features of the landmarks in order to make decisions that lead to effective placement of incisions at selected locations in the capsule 408.

Figure 6:
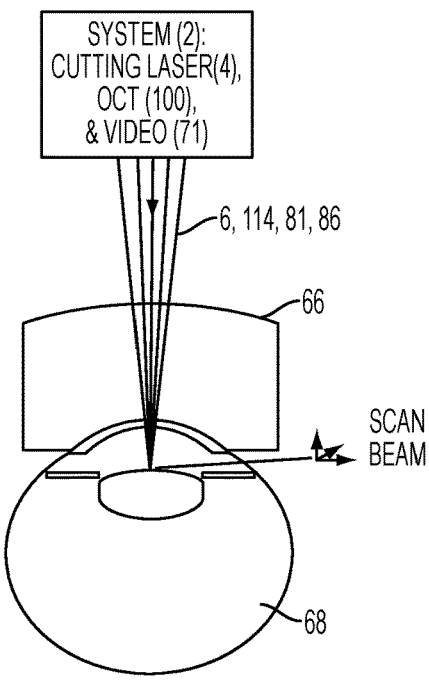
FIG. 6 shows the relationship of the beam paths corresponding to the cutting laser, the OCT, and the video sub-systems relative to the eye.

FIG. 6 is a simplified schematic showing the relationship of the beam paths corresponding to the cutting laser 4, the OCT 100, and the video 71 sub-systems of system 2 relative to the eye 68. The UF beam path 6, the OCT beam path 114, the video beam path 81, and the video illumination beam path 86 are ideally overlaid at the targeted cut location in the eye or at least a relative spatial relationship amongst the paths at the targeted cut location is known via calibration, model, measurement, or some other method. The contact lens 66 which serves as the interface between the system and lens is also shown. All four beam paths have access to a volume within the eye. For the UF beam 6, lateral movement is achieved via galvos 52, 54, for example. The axial or z movement of the focus of the UF beam is achieved via a galvo mechanism 40. The focus of the UF beam thereby is scanned 3-dimensionally throughout a volume within the eye. This scan volume enables the UF laser to access and cut the capsule given a wide range of biological variation. Similarly for the OCT beam 114; its focus can be scanned 3-dimensionally throughout the volume using galvos 52, 54, and 40. The system 2 as in FIGS. 1 & 2 has the ability to scan the focus of the OCT beam throughout the volume to increase signal-to-noise. The focus of the OCT can also remain axially fixed (i.e. in Z) as in the OCT system 156 of FIG. 4. In this case, the depth of operating range in Z for the OCT is large. In either case, the OCT can detect structures that include the contact lens, the cornea, the iris, and the lens throughout a volume.

For the video or viewing subsystem 71 including the video illumination path 86 and camera light path 74 an image of a plane within in the eye is relayed to a detector array, preferable a 2-D detector array. A specific plane within the eye volume can be brought into focus at the detector plane. This focusing ability may be fixed or adjustable. For example the plane containing the inside diameter of the iris could be brought into video focus. Image processing can then be used to determine the boundary of the iris. With proper calibration, modeling, or other method this image analysis can be translated to diameter and center location for the iris within the eye. Other structures at other planes throughout the volume within the eye can be similarly determined by virtue of the depth of focus of the video system or by adjusting the focal plane of the video system.

Figure 7:
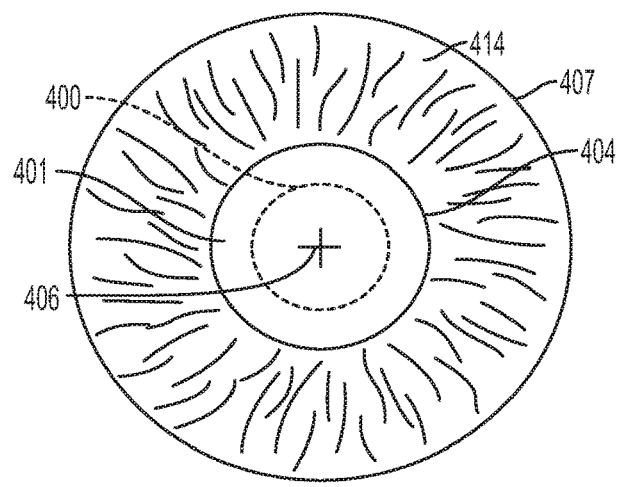
FIG. 7 is an en face schematic of the eye depicting the iris, the iris boundary, the targeted capsulotomy incision location and the center of the incision.
Figure 8:
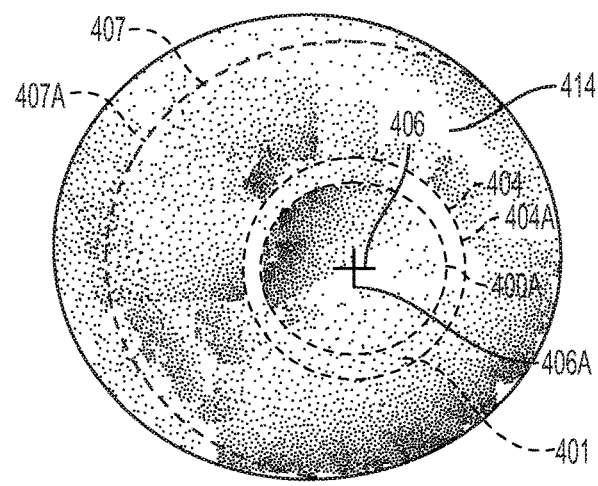
FIG. 8 is an en face image captured from the system's user interface depicting the video image of the patient's eye overlaid with the detected iris boundary and the intended capsulotomy incision.

FIG. 7 is an en face schematic of the eye depicting the iris 414, the iris boundary 404, the capsulorhexis incision location 400 and the center of the iris 406. FIG. 7 shows a schematic representation of the image of a patient's eye 68 as might be captured with imaging system 71, displayed on GUI 304, and used by control electronics 300 for image processing to automatically align incision 400 on capsule 401. FIG. 8 is an actual image frame captured from a GUI display in an implementation of a system 2 as depicted in FIG. 1. The eye image in FIG. 8 is offset within the field of view of the camera (i.e. the image of the eye is not centered) so that the limbus 407 may be more easily seen. In FIG. 8, the demarcations for the limbus 407A, the iris boundary 404A, and the center of the iris 406A that are overlaid onto the video image have been generated by the system via detection and applied algorithm and are provided to guide the user. That is, in FIG. 8 these demarcations are generated by the system 2 and the positions for these demarcations with respect to the image has been automated. These demarcations locations presented via the GUI may be manually manipulated by the user via cursers, touch screen, slide bars, or other user accessible means either initially or as an modification of the automated findings. The capsulorhexis cut location 400 in the capsule can also be determined and presented to the user as demarcation 400A. Interaction of the GUI with the user can thus be two-way: in one way the system presents automated results to the user for review; in the other way the user manipulates or inputs the information for the system to process. For example, by moving the indicated location of the capsulorhexis to a new location, the user is able to reposition the desired location of the capsulorhexis incision. In yet another embodiment, the user is able to modify the indicated location of the iris by translating symbols that represent the system's detected location of the iris. In yet another embodiment the graphical depictions of other cut locations (such as cataract incisions, relaxing incisions, and/or segmentation incisions) may be indicated on the screen, and/or relocated by the user to modify the intended treatment location.

Figure 9:
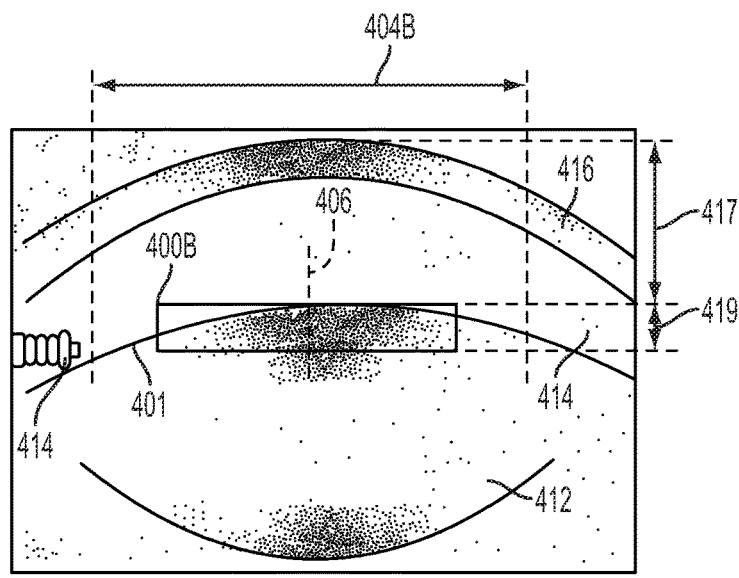
FIG. 9 is an OCT composite image with marked structures and features.

An example of one method to determine the cut location 400A as displayed in FIG. 8 is to determine the iris diameter using the OCT system. Scanning the OCT beam in the volume generates a composite OCT image from the OCT signals. An example of a composite image derived from the OCT is shown in FIG. 9. The iris 414 shows up on both sides of the cross-sectional view. Generally, the inside diameter 404B of the iris can be determined and therefore the center 406 of the iris. The OCT can be used to detect and display the location of the surface of the capsule 401. Using the iris diameter, the center of the iris, and the location of the capsule surface, the location of the entire capsulorhexis cut can be determined.

In yet another embodiment, the location of the capsulorhexis cut is determined by imaging the eye and pupil under a known lighting condition. During treatment, the image is then superimposed on the live image of the eye, and either the fixed image and/or the live image are then translated, scaled, rotated and/or distorted to compensate for differences in the distortion of the lens imaging systems, such that the two images are substantially superimposed. It is then possible to position the intended location of the capsulorhexis and/or any of the other therapies with respect to the pupil in the fixed image.

Figure 17:
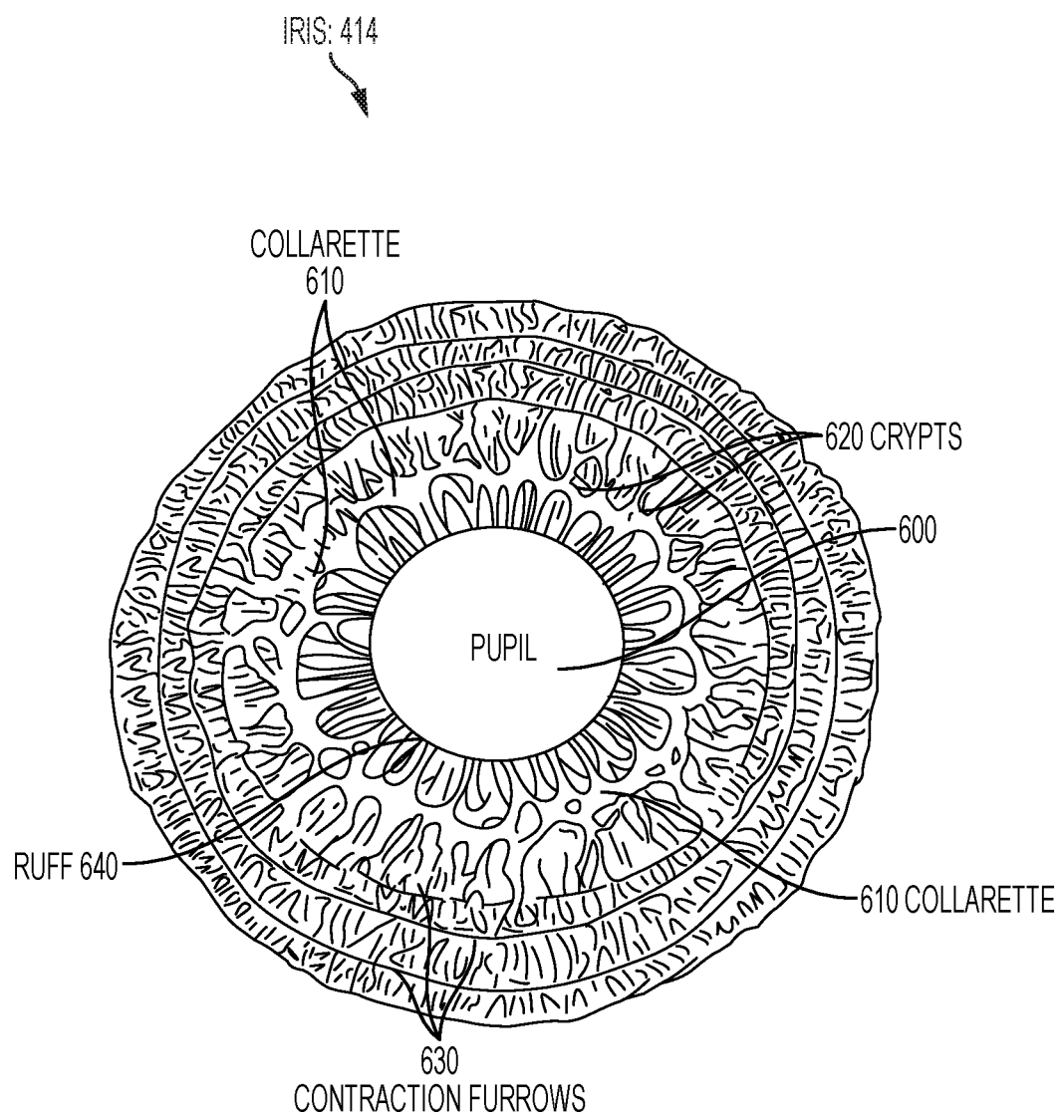
FIG. 17 is a diagram showing the features seen on the anterior surface of the iris.

FIG. 17 is a diagram of the anterior surface of the iris 414 where the papillary zone extends from the pupil 600 to the collarette 610, and the ciliary zone extends from the collarette 610 to the peripheral edge of the iris, where it joins the ciliary body. More specifically, the iris 414 is a pigmented diaphragm with a central aperture, the pupil 600. The iris is suspended in the aqueous humor between the cornea and the lens. The periphery of the iris which is attached to the anterior surface of the ciliary body is called the ciliary margin or root of the iris. The pupil is surrounded by the papillary margin) or inside iris boundary 404 as shown in FIG. 7). The outside diameter of the iris is essentially fixed and measures about 12 mm. The pupil 600 varies in diameter from 1 mm to 9.5 mm depending on a variety of factors including the amount of light entering the eye. Generally the pupil is never fixed and is constantly changing in size in response to the sphincter and dilator papillae muscles. In some portion of the population the left and right pupils differ slightly in size.

The color of the iris varies, e.g. from light blue to dark brown: the color may vary from one eye to another in the same person and in different parts of the same iris. The anterior surface of the iris is divided into a central papillary zone and a peripheral ciliary zone. The line of demarcation is formed by a circular ridge, the collarette 610, which lies about 2 mm from the papillary margin. The collarette may form a wavy line. The anterior surface of the iris is devoid of epithelium and has a velvety appearance. It shows a series of radial streaks caused by trabeculae or bands of connective tissue that enclose the oval-shaped crypts 620 (also known as Fuch's crypts). The trabeculae are most pronounced in the region of the collarette.

Near the outer part of the ciliary region are a number of concentric furrows, which become deeper when the pupil dilates. They generally appear as dark lines and are known as contraction furrows 630 and are caused by the folding of the iris as the pupil dilates. At the pupillary margin, the pigmented posterior epithelium extends anteriorly around the edge of the pupil for a short distance. The epithelium has radial folds, which give its boundary a crenated appearance, sometimes called the ruff 640. Any or all these features of the iris can be used as fiducials under known conditions such as known ambient lighting to mark the location of the iris to be used by the system to locate the capsulorhexis incision. These features include color, color variation, crypts, collarette, ruff, furrows, contraction furrows, trabeculae, radial streaks, bands of connective tissue, and any other discernable feature. All are considered anatomical fiducials.

These fiducials can be recorded using an off-line system or the system's imaging subsystem(s). The ability to employ a physiological image of the anterior portion of the eye under conditions other than those imposed by the system under pre-treatment or treatment conditions allows for location guidance of the capsulotomy incision using information about the eye under natural conditions. The advantage afforded by such a method is to avoid aligning to shifts and distortions in the eye due to conditions imposed by the system or procedure. These shifts and distortions could be a result of pupil dilation, ambient light conditions, patient medication, and head orientation (e.g. cyclorotation, cyclotorsion); and induced by the treatment and pre-treatment lighting conditions, drugs to induce dilation, local or general anesthetic, and patient body orientation. The fiducials can be used by the system to superimpose the natural state image onto the treatment (or pre-treatment) image by employing a number of transformations including translation, scaling, rotation, skew, and other image distortion. A more detailed automated approach to locating the center of the pupil and the entire capsule cut using the OCT system is outlined as follows. As described above, the OCT system produces a 3-dimensional image or map of the anterior segment of the human eye.

This image information is operated upon by any spatial low pass filters such as finite kernel averaging, median filtering and others that are well known to persons skilled in the art, to reduce spurious detection of structures in the eye. The resulting filtered image is thresholded in order to convert the image to a binary image. Alternately, the original image is first thresholded to convert it to a binary image, and then filtered with a spatial lowpass median filter, or any other filter known to those skilled in the art that reduces instances of spurious noise.

Consider each A-scan (a line, sequence, or column of OCT pixels in Z for a given XY location) in the resulting binary image. Furthermore, consider an A-scan to include the concatenation of several A-scans taken at the same XY location, where different depths are used to produce the A-scans. Since the A-scan is registered with respect to the optical system, and since the eye is positioned within a range with respect to the optical system, it is possible to have an a priori range of z positions (depths) at which the various features of the eye will be located (taking into account the known range of physiological variations in the geometry of eye structures among the human population). If the feature or structure to be detected is above the supporting structure of that feature (e.g. the anterior surface of the cornea), the first non-zero pixel (the most negative Z location pixel) in each range of pixels in the column or A-scan of the binary image is taken to be an edge pixel for that surface. Alternately, if the desired surface to be detected is below the supporting structure below the supporting structure of that feature (e.g. the posterior surface of the cornea), then the last non-zero pixel (the most positive Z location pixel) is taken to be an edge pixel. In yet another embodiment, in each of the 2 cases above, the pixel is considered to be an edge pixel if it is the first non-zero pixel and the succeeding n pixels (e.g. n=9) are also non-zero. In any case, its XYZ locations are recorded, thus the image has been reduced to a set of XYZ triples (i.e. each point in the set has an X coordinate, a Y coordinate, and a Z coordinate), each representing the location of an edge pixel in the 3-dimensional OCT image.

These XYZ triples may be fit to a sphere, or any other such mathematical surface. We will use sphere fitting in the following non-limiting example. Each XYZ triple may represent a valid "pixel" on the anterior lens or lens capsule; or each "pixel" may represent systematic or random sources of noise in the OCT system. Therefore to reduce this uncertainty, the XYZ triples are fit to a sphere, using iterative robust least-squares techniques. Iterations are performed where initially the central portion of the eye is fitted to a sphere using a classical least squares technique (in the preferred embodiment the central 15% with respect to the scan radius in the XY directions of the XYZ triples are included). Any of the well-known robust least-squares (LS) techniques are used for weighting edges according to each edge pixel's proximity to the resulting fit, such as bi-square, least trimmed squares, M-estimation, MM-estimation, S-estimation, and others known to those skilled in the art. The robust LS technique is repeated until the robust LS fit solution converges. Finally, more edges from the feature or structure being identified are added (in the preferred embodiment, an additional 5% of the edge pixels), and the robust fitting algorithm is repeated. The steps of adding additional edge pixels and performing additional robust LS fitting is repeated until all XYZ triples have been included in the fit. After all fitting has been completed, in the case of the anterior surface, XYZ triples that have very small weightings (in the preferred embodiment, zero weightings) with positions that are outside the sphere, and have Z components that are more negative than all points on the surface of the sphere can be considered members of the iris set, whereas edge pixels that have relatively large weightings (in the preferred embodiment, non-zero weightings) can be considered members of the pupil set. In the preferred embodiment, the division between pupil and non-pupil pixels is defined by locations in which three or more neighboring non-pupil pixels are located. In this fashion, the OCT system can determine, in 3-dimensions, the location of the pupil, which enables the UF treatment system to dispose the treatment (i.e. cut) while missing the non-pupil (iris) locations.

The above concept can be extended to include the identification of other surfaces, features, or structures. The limbus, which is defined as the transition from the cornea to the sclera, or the corenoscleral junction, can be identified during the fitting of the cornea anterior: the outliers that cluster outside the central fit region, and are closest to the central region can be considered in the transition zone between the cornea and the sclera. Similarly, if a sphere is fit on the globe of the eye (of the sclera, beyond the limbus), then the outliers that cluster central to the globe of the eye can be considered to be members of the non-globe family, and the boundary between the globe and the central cluster can be defined as the limbus. When fitting the cornea posterior, the anterior chamber angle (where the iris joins the scleral spur) can be identified as the peripheral outliers in a spherical fit to the cornea posterior. This information may be used to guide the placement of the capsulotomy and/or and corneal incisions, such as the cataract instrument, paracentesis, and astigmatic relaxing or correcting incisions. In this way we also may locate the boundary as defined by the intersection of adjacent structures; such as the limbus as determined by the junction of the anterior cornea and the sclera, the pupil as determined by the junction of the lens and iris, the limbus as determined by the junction of the posterior cornea and the iris.

Generally, the capsulorhexis cut diameter is pre-determined using other factors such as the diameter of the intended IOL. But this pre-determined capsulorhexis diameter can be checked against the iris diameter found automatically as described previously. The cut may proceed in a go-no go fashion or a desired scaling margin implemented relative to the automatically found iris boundary. The 3-dimensional information from the OCT is an advantage over 2-dimensional, e.g. XY, systems which must approximate the third dimension, e.g. Z, by assuming a nominal depth for the iris, or derive a depth of the iris from another imaging modality.

Generally in practice, the entire capsulorhexis cut is not restricted to a single plane or a single layer in Z. The cut can be described as having a cylindrical shape (extruded circle or ellipse) as opposed to a flat circle. As depicted in FIG. 9, the entire cut circumscribes a volume with a Z location 417 and a depth thickness 419. There is an extent to the cut in Z, i.e. the depth thickness 419, in order to take into account variations in the depth of the targeted capsule cut locations throughout the entire cutting procedure. These variations can arise from tilt of the capsule, decentration of the capsule, movement of structures, and tolerances in the UF, OCT, & video systems. The process of cutting the capsule involves stepping an amount 419 in depth to ensure that the capsule is intersected by the cutting mechanism (e.g. the plasma) generated by the UF beam. The OCT generates both lateral (XY) and depth (Z) information (3-dimensional). The resolution for the Z information can be at the level of 10 um using common OCT configurations with approximately 100 nm wavelength bandwidth. The high resolution depth information from the OCT allows for minimizing the depth thickness 419 of the cut. This is turn reduces the cutting processing time. The relatively high resolution 3-dimensional information from the OCT is an advantage over 2-dimensional system. 2-dimensional systems must approximate with large margin the third dimension Z by assuming a nominal depth for the iris, depth of the capsule, tilt of the capsule, decentration of the capsule, and radius of curvature of the capsule or derive these and similar quantities from other measurement modalities. The 3-dimensional information from the OCT can be used to project the 2-dimensional circular path of the desired capsulorhexis onto the surface of the sphere that represents the anterior surface of the lens in order to produce a 3-dimensional path for the cutting of the capsulorhexis.

The system also provides for user input of diagnostic information relating to the patient anatomy, such as that acquired by pre-operative AC OCT, Ultrasound, or any other such diagnostic test that provides information about the patient's central lens thickness, lens curvatures, anterior chamber depth, corneal thickness, etc. The system may use these values as expectation values and/or to replace or augment its own acquisition of 3D information. As a non-limiting example, this information may be used for lens and/or capsule pattern depth settings when utilizing the anterior chamber depth and central lens thickness obtain preoperatively. This information allows the system to augment its own internal imaging results and/or verify them. For example, by knowing the patient's anterior chamber depth and determining the location of their cornea, the system can limit the axial extent of a capsulotomy pattern. Similarly, entering the lens thickness allows the system to plan for a lens phacofragmentation pattern axial extent. Adding the anterior chamber depth to the lens thickness further allows the system to determine the pattern depth placement. Combine this with the lens surface curvatures, or a conservative estimate of them (such as 8 mm for the lens anterior and 5.5 mm radius for the lens posterior surface) may be used to completely define the pattern and its placement. Of course, the axial (depth) extent of the pattern will require large anterior and posterior surface safety margins. Integrated imaging will provide improved results. However, the above-mentioned techniques may provide a contingency in the case of insufficient imaging data for more automated feature detection.

Although the above description of iterative robust least squares sphere fitting is taught in the context of fitting the anterior surface of the crystalline lens, it can also be used for determining the best fit sphere to each of the following structures: the cornea anterior, the cornea posterior, and the lens posterior. In the case of these three additional structures, the use of the weightings to determine the iris location may not be applicable. In other words, the OCT can be used to detect structures or features other than those associated with the iris for the purpose of directing the location for the cutting laser. Instead of using the center of the iris to center the cut, the axis of the lens can be used as a guide for the centering. The axis of the lens can be determined by detecting the anterior and posterior surfaces for the lens using the OCT, calculating radii of curvature near the vertex for these surfaces, then connecting the centers of these radii to establish an axis. The intersection of this axis with the surface of the capsule can then be chosen as the center of the capsulotomy (or capsulorhexis) cut. Likewise the surfaces of the cornea can be used to determine the axis or a best-fit match through the center of radii of the more than 2 surfaces can be used. The diameter of the capsulorhexis cut may also be chosen differently. The diameter of the cut may be simple ratio of the iris diameter. The cut may also have a non-circular shape in the XY direction. It could follow the contour of the iris diameter, for example.

Alternatively, the location of the capsulorhexis incision 400 can be determined using the video system. Features such as the iris can be found using a video image such as that shown in FIG. 8. For example, there are numerous image processing approaches to locating center 406 of iris 414 such as: Canny, Laplacian, and/or Sobel edge detection schemes, adaptive thresholding and subsequent morphological interpretations, including binary determinations. Noise in the sensing system may be reduced by 1-dimensional or 2-dimensional image filtering techniques such as Gaussian windowing, Bartlett windowing, or simple moving average windowing. All are considered within the scope of the present invention. Specifically, an example using the video image follows. We define the pupil as the area inside iris boundary 404. Methods for determining the center of the pupil include performing edge detection on the iris boundary 404 and fitting a circle, ellipse, or other closed curve to the boundary between pupil and iris; segmenting pixels into pupil and non-pupil pixels, and finding the centroid of the pupil, then maximizing the circle and/or ellipse that can fit inside the pupil; again segmenting the pixels into pupil and non-pupil pixels, finding the centroid of the pupil, then alternately a) maximizing the circle and/or ellipse that can fit inside the pupil, and b) moving the center of the circle in a direction opposite the direction of the closest non-pupil pixel with respect to the center of the circle/ellipse. This iterative procedure is repeated until no further improvement in circle or ellipse size can be made. Once the iris boundary and center are found, the capsule cutting process may proceed. The cut diameter may be pre-determined by IOL requirements and checked for fit with respect to the iris diameter as determined through the image processing for edge detection of the video information. Likewise for the center of the cut; it can be determined using the center for the iris boundary as determined by the previously described processing of the video image. The absolute depth location 417 and depth thickness 419 of the cut as illustrated in FIG. 9 can be determined by depth of focus of the video system or active focusing of the video system or by conjecture based on statistical anatomical data relating the iris to the capsule. The depth thickness 419 can be increased to account for a larger range of expected variations using these techniques. The larger depth thickness may result in a longer duration for the cutting time.

Patients often have eccentric pupils, and the limbus 407, which may be distinctly recognizable in a video image, is also considered as a means to discern the geometric center of the capsule 401. Capsule 401 is held in place by zonules (not shown) that connect to the ciliary's apparatus (not shown) directly beneath the limbus 407. However, when iris 414 is widely dilated, it is nominally concentric with the limbus 407, thus producing an equivalent measure. The aspects of the capsulorhexis cut as described in FIG. 10 that includes the cut diameter, the center of the cut, the depth 417, and the depth thickness 419 can be achieved using video information derived using limbus recognition.

In yet another embodiment, both the OCT and video system can be used to guide the capsule cutting. For example, the center of the pupil can be determined by simultaneously considering both the OCT and the video system data to determine if a pixel or eye location is a pupil or non-pupil pixel. For a location to be deemed as within the pupil, it may be required that both systems independently discern this conclusion. Alternatively, the location can be within the pupil if at least one system comes to this conclusion. In either case, information from both systems is considered.

Figure 10:
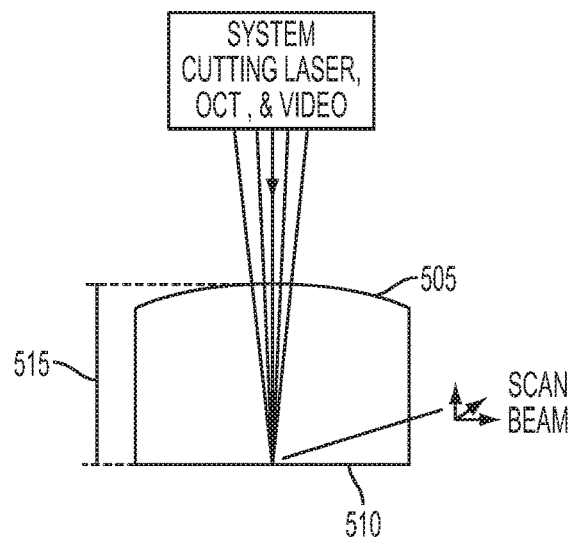
FIG. 10 is the optical layout indicating a calibration lens with target surface.

The imaging system and UF beam 6 must be registered. The imaging system can be the video system, the OCT system 100 or a combination of both. Thus, a spatial calibration of system 2 must be achieved to accurately place cuts. This can be achieved in a variety ways, and all are considered within the scope of the present invention. FIG. 10 is the optical schematic indicating a calibration lens 505 with a target surface 510. The calibration lens 505 is made of a material of known refractive index, thickness 515, and optical power.

It serves as a stand-in or surrogate for the eye. The thickness, material, & shape are chosen such that the there is a known relationship between the dimensions at the target location 510 to the dimensions in the eye. Surface 510 can consist of a reticle or mask with known calibrated dimensions. An optical calculation via an optical design code such as Zemax, OSLO, & CODE V can be used to further refine the relationship between the calibration lens and reticle dimensions with respect to the eye. Factors that may be included in this refinement include calibration lens 505 index, thickness, shape and anticipated eye optical factors such as cornea thickness, cornea index, cornea surfaces radii, aqueous index, aqueous thickness, and crystalline lens index, crystalline lens thickness, and crystalline surfaces radii.

Figure 11:
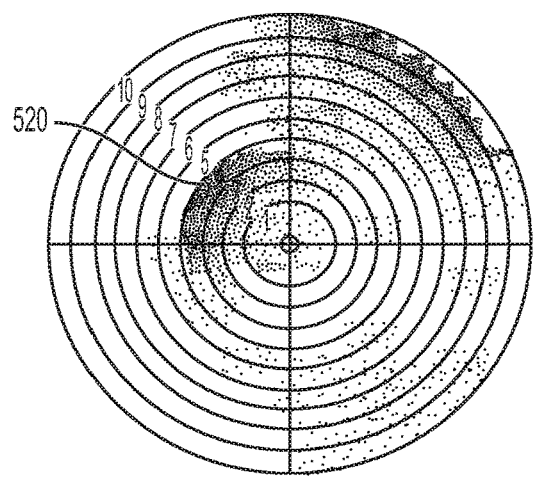
FIG. 11 is a video image of a reticle target used to calibrate the video.
Figure 12:
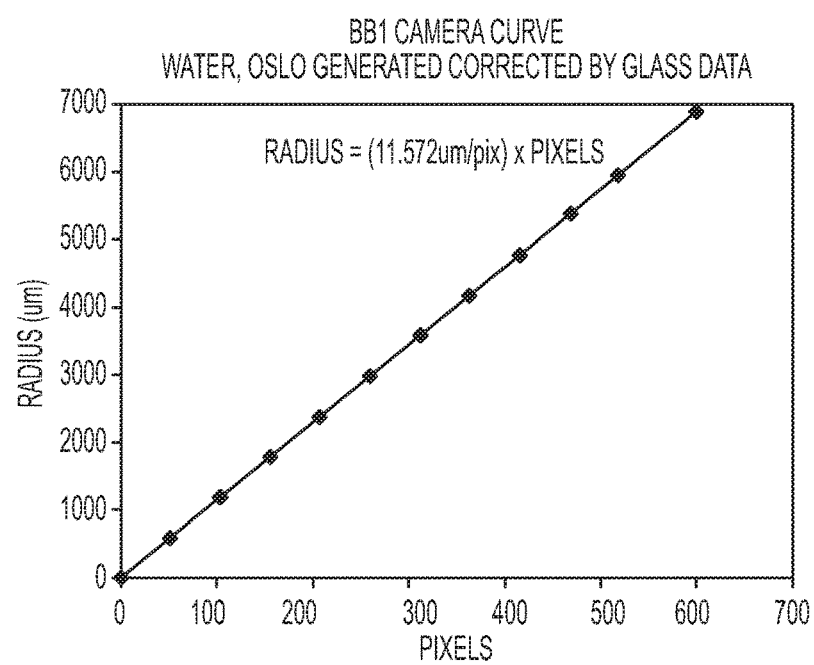
FIG. 12 is an example of a video calibration curve mapping video pixels to corresponding physical dimensions in the eye.
Figures 13, 14:
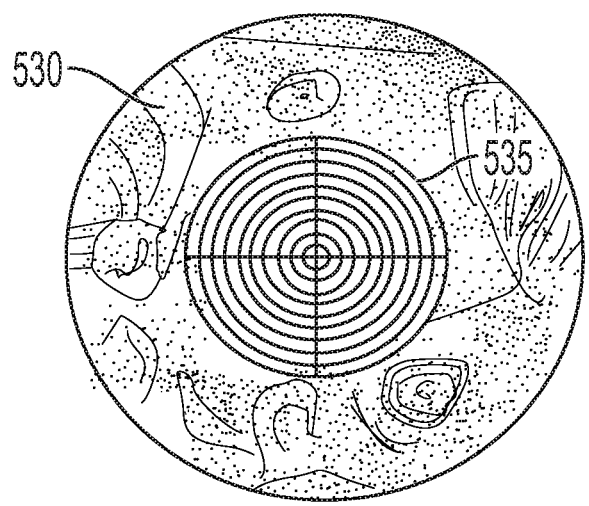
FIG. 13 is video image of a mark or burn pattern created by the cutting laser in a calibration target used to register the cutting laser placement, the OCT detection, and the physical dimensions of the eye.
FIG. 14 is table of the critical calibration factors including pixel scaling, center location, and rotation used to register the cutting laser, OCT, and video image to physical dimensions in the eye.

Using this reticle, the pixels can be mapped to eye dimensions as in the video case and the scanned OCT signal can be related to the eye dimensions as in the OCT case. FIG. 11 is an example of a reticle image as viewed using the video system. In this case the reticle is a chrome masked glass surface with circles 520 of known diameter. In the image of FIG. 11 the circles are labeled in millimeters. Video pixels to reticle millimeters can then be calibrated. The image millimeters can be related to equivalent eye dimensions at the designated plane in the eye. This relation can be assisted via optical modeling. An example of a curve that relates video pixels to eye dimensions is given in FIG. 12. Similarly the UF beam can be calibrated against a reticle surface 510 as in FIG. 10. Telecentricity in the eye space of the video and UF beams enables the calibration curve as in FIG. 12 to be effectively applied throughout the cutting volume within the eye FIG. 13 is another example of a calibration technique to register the imaging system to the UF beam. In FIG. 13, the target surface is made from a material 530 such as a thin piece of Mylar that can be marked 535 or burned by the focused UF beam. Once marked, the OCT can detect the mark locations. The OCT is thereby registered to the UF beam.

Additionally if this marked material is viewed using the video system as in FIG. 13, then the video pixels can be registered to the UF and therefore the OCT beam locations. Relating back to physical eye dimensions can be achieved by using the calibration technique as described for the calibration target used FIG. 11 and the calibration curve as in FIG. 12. Using a target material that can be marked by the UF beam, read by the OCT and video systems, and calibrated to physical eye dimensions yields not only scaling information as shown as the curve slope in FIG. 12 but also the center and rotation of the UF beam marking pattern with respect to the imaging (video & OCT) systems. An example of the full repertoire of calibration information from such calibration techniques is given in the table of FIG. 13.

FIG. 14 is table of the critical calibration factors including pixel scaling, center location, and rotation used to register the cutting laser, OCT, and video image to physical dimensions in the eye. There will be a set of values for the cutting laser and for the OCT, but ideally the OCT and the cutting laser overlap so that only ones set is necessary as shown in FIG. 14.

Figure 15:
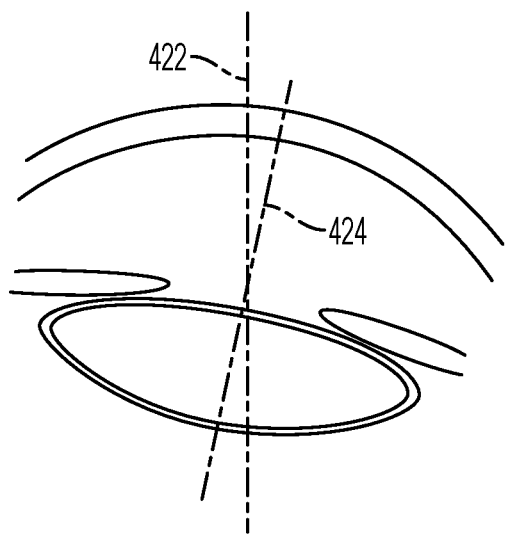
FIG. 15 is a cross-sectional schematic of the eye showing a tilted capsulotomy incision plane.

FIG. 15 is a cross-sectional schematic of the eye showing a tilted capsulorhexis incision plane. Its shows a tilted lens and ideally the cut for the capsule will follow this tilt. Here OCT system 100 of FIG. 1 is used to discern capsule 401 by detecting surfaces 408 & 410 of lens 412. The OCT system can detect this tilt by finding the axis 424 connecting the centers of curvatures of the anterior and posterior lens surface. The tilt of this axis 424 can be seen relative to an axis 422 defined by the center of the iris and coincident to the system's optical axis. Similarly, misalignment between system 2 and eye 68 can be accounted for using OCT system 100, as well. The OCT system is generally superior in detecting relative tilt information between the eye and the system as compared to a video system that may have a relatively large depth of focus and therefore difficulty in distinguishing the tilt component.

Figure 16:
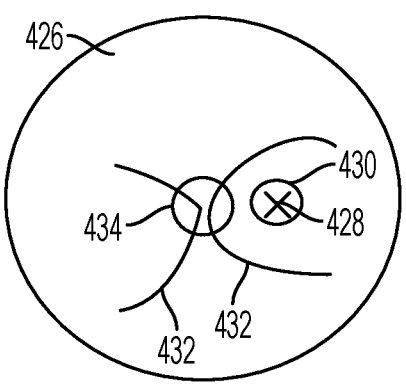
FIG. 16 shows a schematic representation of a retinal image.

FIG. 16 shows a schematic representation of a retinal image. The inclusion of retinal structure (e.g.: the foveola or the fovea centralis) allows for better centration about the visual axis it specifies. To accomplish this, an adjustable focus system may be placed in the imaging system 71 to allow it to image both the iris and the retina. The focal shift between the image of the iris and the retina will describe the length of the eye, and this may further be used to calculate the angle between the crystalline lens center, or other point such a optical cardinal point of the lens, and the retinal registration feature as well as the offset of incision 400 on capsule 401. Such an adjustment could be achieved by using a calibrated z-adjust similar z-adjust 40 in the description of FIG. 1. Furthermore, increasing the diameter of aperture 81 in imaging system 71 will reduce its depth of focus, and thus better locate the true position of ocular structures such as retina 426 and iris 402. Again, image processing could then locate center 406 within pupil 404 (or iris 402 or limbus 407) and center 428 within fovea 430, register them and thus discern the visual axis of the eye. This could then serve as the axis for capsulorhexis centration, in lieu of centerline 422. Likewise, an OCT system could be made to discern both the iris and retinal structures for such determination. A fixation light may also be used to aid in said retinal/ocular alignment.

Although the typical values for the thickness of lens 412 (3-5 mm) and the angular difference between the geometric and visual axis (3-7°) only yields a worse case displacement of center 406 of ~600 µm, it is well within the accuracy of the present invention, as described herein. Furthermore, the use of near-infrared light for imaging system 71 simplifies detection by providing enhanced return signals that might otherwise be more attenuated due to the presence an optically opaque cataract The system may also provide the user the choice of using any one of the abovementioned fits to place the laser created incisions. For example, the video system may display an en-face image of the patient's eye with the limbal, geometric, and visual centering results overlaid. The user may then choose the method based upon its appearance with respect to the video image. Similarly, the system may display the intended location(s) of corneal incisions for the user to choose.

Figure 18:
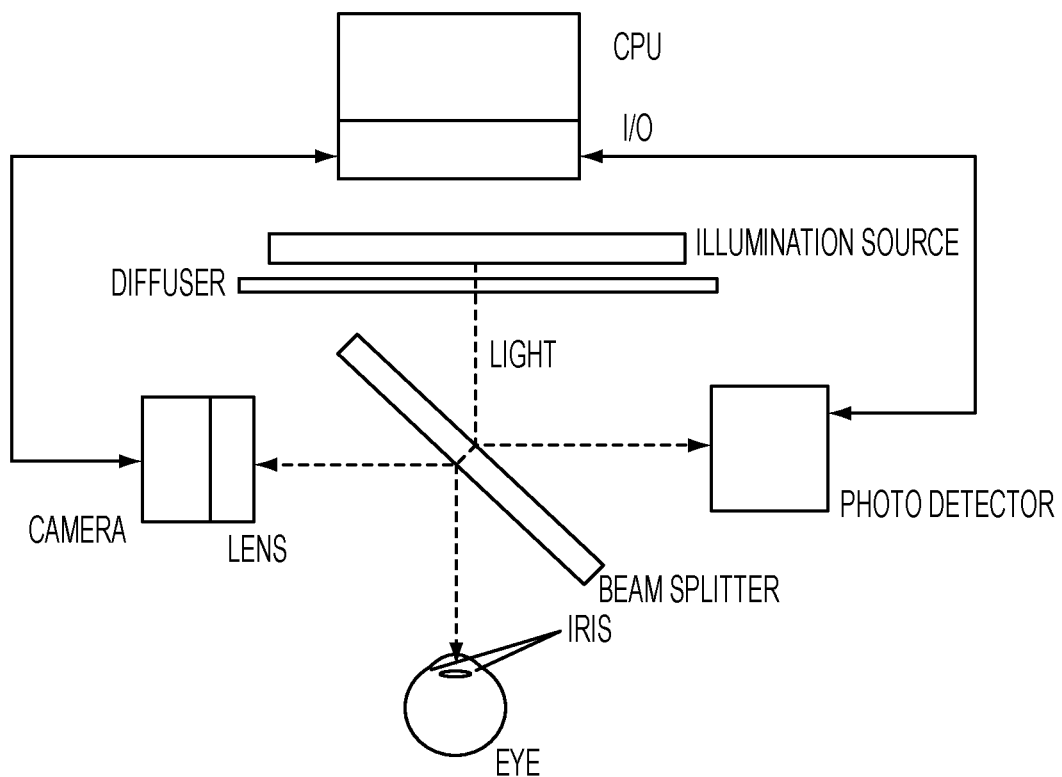
FIG. 18 is a diagram of an apparatus for measuring the pupil of a patient under ambient lighting conditions.
Figure 19:
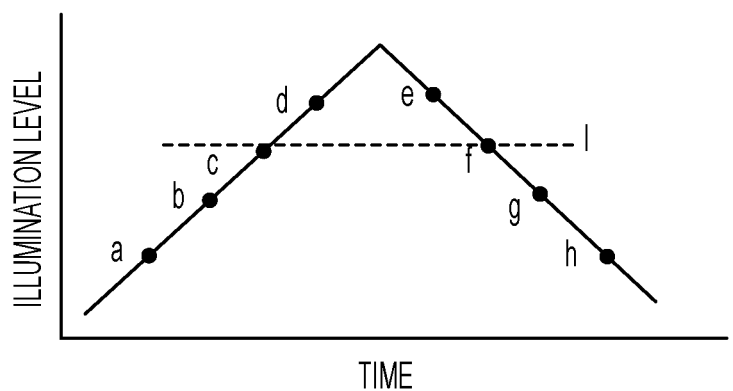
FIG. 19 is an example of a illumination level ramp.
Figure 20:
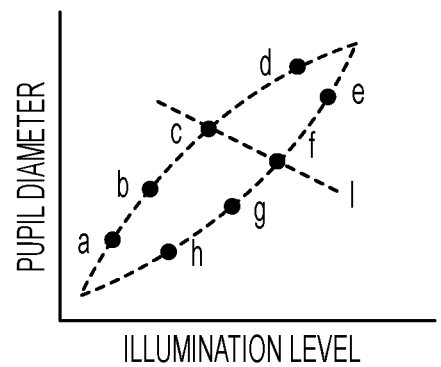
FIG. 20 is an example of the pupil diameter data gathered from iris images.
Figure 21:
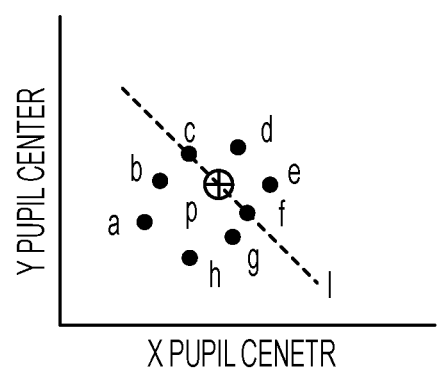
FIG. 21 is an example of the pupil centroid data gathered from iris images.

FIG. 18 shows an embodiment of a device for measuring the physiologic pupil as it responds to varying lighting conditions. The amount of light provided by the illumination source may be diffused by the diffuser to provide a more uniform light distribution incident upon the eye of the patient under test. Beamsplitter provides active feedback of the level of illumination light via the photodetector while simultaneously imaging the iris of the eye using the camera. All of these electronic elements may be connected to a CPU via the I/O port. This configuration provides a very flexible instrument to measure the pupil size, shape and centroid as a function of illumination level. As such, it may be calibrated to adjust the illumination level across a range corresponding to typical ambient lighting conditions that vary from a dark night to a bright sunlit day, passing through the typical 800 lux of an office environment. The illumination source may also be made to provide for varying the spectral components of the light to augment the measurement. The rate of change of the illumination intensity can be made to vary a rate that accommodates the physiological pupil response in order to accurately capture the pupil response, as is schematically shown in FIG. 19. Data containing the pupil size (FIG. 20) and centroid location (FIG. 21) vs. illumination level may be made to provide the information necessary to best locate the lateral or transverse position of the capsulotomy incision. In the example figures, levels identified by indicia a-h correspond to practical situations, such as morning light, etc. Line I connects the data c-f, the illumination level deemed appropriate for the patient under test. Pupil response may exhibit a certain amount of hysteresis, as shown in FIGS. 20 & 21. Thus, the center point of line I, point P, is used to define the median capsulotomy incision center location for that ambient light level. The present invention will also capture images of the dilated pupil for use in intra-operative registration, as described in detail above.

What is claimed is:

1. A system for cataract surgery on an eye of a patient, comprising:
   a. a laser source configured to produce a treatment beam comprising a plurality of laser pulses;
   b. an integrated optical system comprising an Optical Coherence Tomographer (OCT) coupled to a treatment laser delivery assembly such that the OCT and the treatment laser delivery assembly share at least one common optical element, the integrated optical system being configured to acquire image information pertinent to one or more targeted tissue structures and direct the treatment beam in a 3-dimensional treatment pattern to cause breakdown in at least one of the targeted tissue structures;
   c. a patient support configured to maintain the eye of the patient within a range of the optical system; and
   d. a controller operatively coupled to the laser source and the integrated optical system, and configured to:
      1) adjust the treatment beam and the treatment pattern based upon the image information,
      2) operate the OCT to perform one or more A-scans of at least one anatomical structure of the eye at each of a plurality of XY locations, thereby obtaining image information of a predetermined range of Z locations at each of the plurality of XY locations,
      3) identify a plurality of candidate edge locations for the at least one anatomical structure of the eye in a form of XYZ triples by identifying either a first non-zero pixel or a last non-zero pixel in each predetermined range of Z locations for each of the plurality of XY locations,
      4) fit a mathematical surface model to the candidate edge locations by first fitting a first set of the candidate edge locations consisting only of those candidate edge locations which are located in a central region of the plurality of XY locations to the mathematical surface model by performing an iterative least-squares fit algorithm until a solution of the iterative least square fit algorithm converges to produce a first set of fit candidate edge locations,
      5) process the image information based on proximity to the mathematical surface model to identify a second set of candidate edge locations for the at least one anatomical structure, the second set of the candidate edge locations being located outside the central region of the plurality of XY locations, and adding the second set of the candidate edge locations to the first set of fit candidate edge locations, and repeating the iterative least-squares fit algorithm to fit a combined set of the first set of fit candidate edge locations and the second set of the candidate edge locations to the mathematical surface model, thereby identifying a boundary of the at least one anatomical structure.

2. The system of claim 1, wherein the at least one anatomical structure comprises a cornea.

3. The system of claim 1, wherein the at least one anatomical structure comprises a sclera.

4. The system of claim 1, wherein the at least one anatomical structure comprises a limbus.

5. The system of claim 1, wherein the at least one anatomical structure comprises an iris.

6. The system of claim 1, wherein the at least one anatomical structure comprises a lens.

7. The system of claim 1, wherein the at least one anatomical structure comprises a lens capsule.

8. The system of claim 1, wherein the mathematical surface model is a spherical surface.

9. The system of claim 1, wherein the mathematical surface model is an aspherical surface.

10. The system of claim 1, wherein the controller is further configured to locate two or more boundaries between a corresponding three or more anatomical structures from among the at least one anatomical structure of the eye.

11. The system of claim 10, wherein the boundaries include an intersection between a cornea of the eye and a sclera of the eye.

12. The system of claim 10, wherein the boundaries include an intersection between a cornea of the eye and an iris of the eye.

13. The system of claim 10, wherein the boundaries include an intersection between a lens of the eye and an iris of the eye.

14. The system of claim 1, wherein the controller is configured to utilize rejected candidate edge locations of a least-squares fit analysis to identify the at least one anatomical structure of the eye.

15. The system of claim 1, wherein the boundary is disposed between a second boundary surface portion that completely surrounds a first boundary surface portion.

16. The system of claim 1, wherein the image information is reduced to include the candidate edge locations prior to fitting the mathematical surface model.

17. The system of claim 1, wherein a candidate edge location from among the plurality of candidate edge locations is identified as the first non-zero pixel when the at least one anatomical structure to be detected is above a supporting structure of the at least one anatomical structure.

18. The system of claim 1, wherein a candidate edge location from among the plurality of candidate edge locations is identified as the last non-zero pixel when the at least one anatomical structure to be detected is below a supporting structure of the at least one anatomical structure.

19. The system of claim 1, wherein the central region comprises a central 15% of the XY locations.

* * * * *